United States Patent
Salvucci

[11] Patent Number: 5,115,648
[45] Date of Patent: May 26, 1992

[54] ANXIETY TRANSFERENCE RING ORGANIZATION

[76] Inventor: Anthony J. Salvucci, 10388 Red Fir Rd., P.O. Box 898, Truckee, Calif. 95734

[21] Appl. No.: 680,125

[22] Filed: Apr. 3, 1991

[51] Int. Cl.⁵ .............................................. A44C 9/00
[52] U.S. Cl. .......................................... 63/15; 242/96
[58] Field of Search .................... 242/85, 96; 223/101, 223/106; 112/80; 63/1.1, 2, 15, 15.5, 15.45, 15.8; 224/217, 218, 219, 162

[56] References Cited

U.S. PATENT DOCUMENTS

| | | | |
|---|---|---|---|
| 1,213,102 | 1/1917 | Hill | 224/162 X |
| 1,672,355 | 6/1928 | Ullman | 63/1.1 |
| 2,753,130 | 7/1956 | Sjögren | 242/96 |
| 3,596,964 | 8/1971 | Zazzara | 224/217 X |
| 3,605,437 | 9/1971 | Litton | 63/1.1 |
| 3,952,965 | 4/1976 | Falcon | 242/96 |
| 4,084,692 | 4/1978 | Bilweis | 224/217 X |
| 4,715,554 | 12/1987 | Kuntze | 242/96 X |
| 4,807,347 | 2/1989 | Johnson | 242/96 X |
| 4,826,100 | 5/1989 | Bellineau | 242/85 X |
| 4,844,308 | 7/1989 | Porteous | 224/217 |

*Primary Examiner*—Renee S. Luebke
*Assistant Examiner*—Jerry Redman
*Attorney, Agent, or Firm*—Leon Gilden

[57] ABSTRACT

An organization to therapeutically provide an alternative nervous nail-biting habit into a harmless biting and chewing of an extensible and retractable fishing line member rotatably mounted within a spool within a ring organization, whereint he ring organization includes a cap securable to a base with the cap including a floor mounting an abrasive plate surrounded by a protective wall to provide for fingernail grooming in lieu of a nail-biting habit. The fishing line is utilized as a biting alternative.

1 Claim, 4 Drawing Sheets

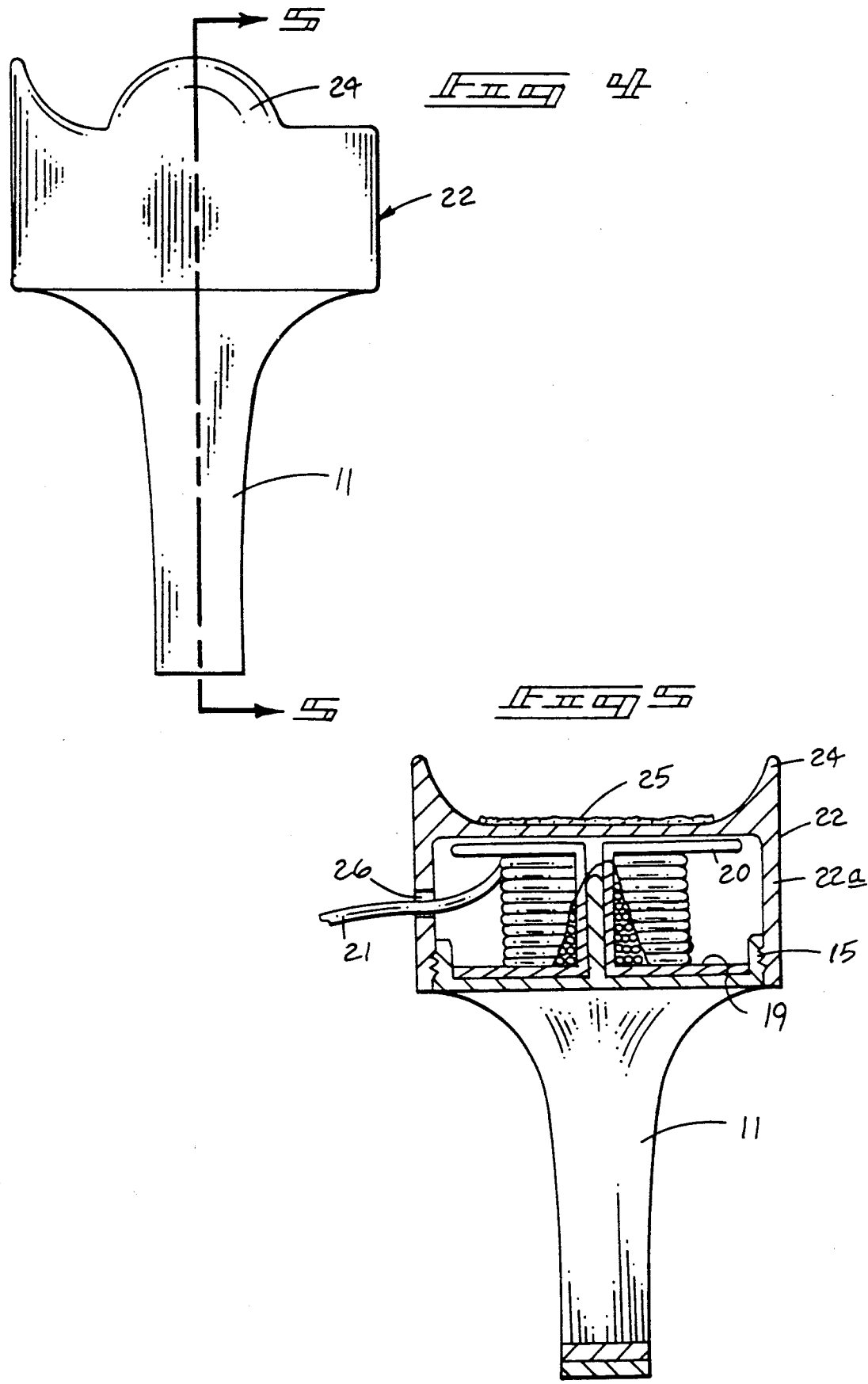

ANXIETY TRANSFERENCE RING ORGANIZATION

BACKGROUND OF THE INVENTION

1. Field of the Invention

The field of invention relates to therapeutic devices, and more particularly pertains to a new and improved anxiety transference ring organization wherein the same provides an individual a finger-mounted ring organization to provide a convenient and readily accessible alternative biting member providing for a fishing-line type element to be extracted from the ring structure through an opening in the cap of the ring organization.

2. Description of the Prior Art

Rings of various types have been utilized in the prior art for convenience of storage of various devices. The instant invention sets forth a ring organization to provide a therapeutic and medially advantageous alternative to unnecessary and unpleasant nail biting by individuals to permit the individuals to cease undesirable nail biting habits.

Examples of prior art ring structure may be found and exemplified in U.S. Pat. No. 4,187,697 to Castelo wherein a ring structure includes a drill mounting removably and slidably mounted within the ring structure.

U.S. Pat. No. 4,821,533 to Bonnefoy sets forth a ring member utilizing a unique manner of setting jewels within the ring member.

U.S. Pat. No. 4,742,696 to Jenkins sets forth a ring member with a cap pivotally mounted to the ring for replacement of various stones secured within the ring by the cap.

U.S. Pat. No. 4,764,140 to Wood sets forth a Mexican jumping bean toy setting forth a ring mounting a jumping bean type organization therewithin.

As such, it may be appreciated that there continues to be a need for a new and improved anxiety transference ring organization as set forth by the instant invention which addresses both problems of ease of use as well as effectiveness in construction in providing an alternative nail-biting object for use by individuals in attempting to cease nail-biting habits and in this respect, the present invention substantially fulfills this need.

SUMMARY OF THE INVENTION

In view of the foregoing disadvantages inherent in the known types of ring apparatus now present in the prior art, the present invention provides an anxiety transference ring organization wherein the same sets forth nail grooming structure and a line member to address anxiety of a nail biting individual. As such, the general purpose of the present invention, which will be described subsequently in greater detail, is to provide a new and improved anxiety transference ring organization which has all the advantages of the prior art ring structure and none of the disadvantages.

To attain this, the present invention provides an organization to therapeutically provide an alternative nervous nail-biting habit into a harmless biting and chewing of an extensible and retractable fishing line member rotatably mounted within a spool within a ring organization, wherein the ring organization includes a cap securable to a base, with the cap including a floor mounting an abrasive plate surrounded by a protective wall to provide for fingernail grooming in lieu of a nail-biting habit. The fishing line is utilized as a biting alternative.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved anxiety transference ring organization which has all the advantages of the prior art ring structures and none of the disadvantages.

It is another object of the present invention to provide a new and improved anxiety transference ring organization which may be easily and efficiently manufactured and marketed.

It is a further object of the present invention to provide a new and improved anxiety transference ring organization which is of a durable and reliable construction.

An even further object of the present invention is to provide a new and improved anxiety transference ring organization which is susceptible of a low cost of manufacture with regard to both materials and labor, and which accordingly is then susceptible of low prices of sale to the consuming public, thereby making such anxiety transference ring organizations economically available to the buying public.

Still yet another object of the present invention is to provide a new and improved anxiety transference ring organization which provides in the apparatuses and methods of the prior art some of the advantages thereof, while simultaneously overcoming some of the disadvantages normally associates therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an orthographic side view, taken in elevation, of the instant invention.

FIG. 5 is an orthographic view, taken along the lines 5—5 of FIG. 4 in the direction indicated by the arrows.

DESCRIPTION OF THE PREFERRED EMBODIMENT

Figure 1:
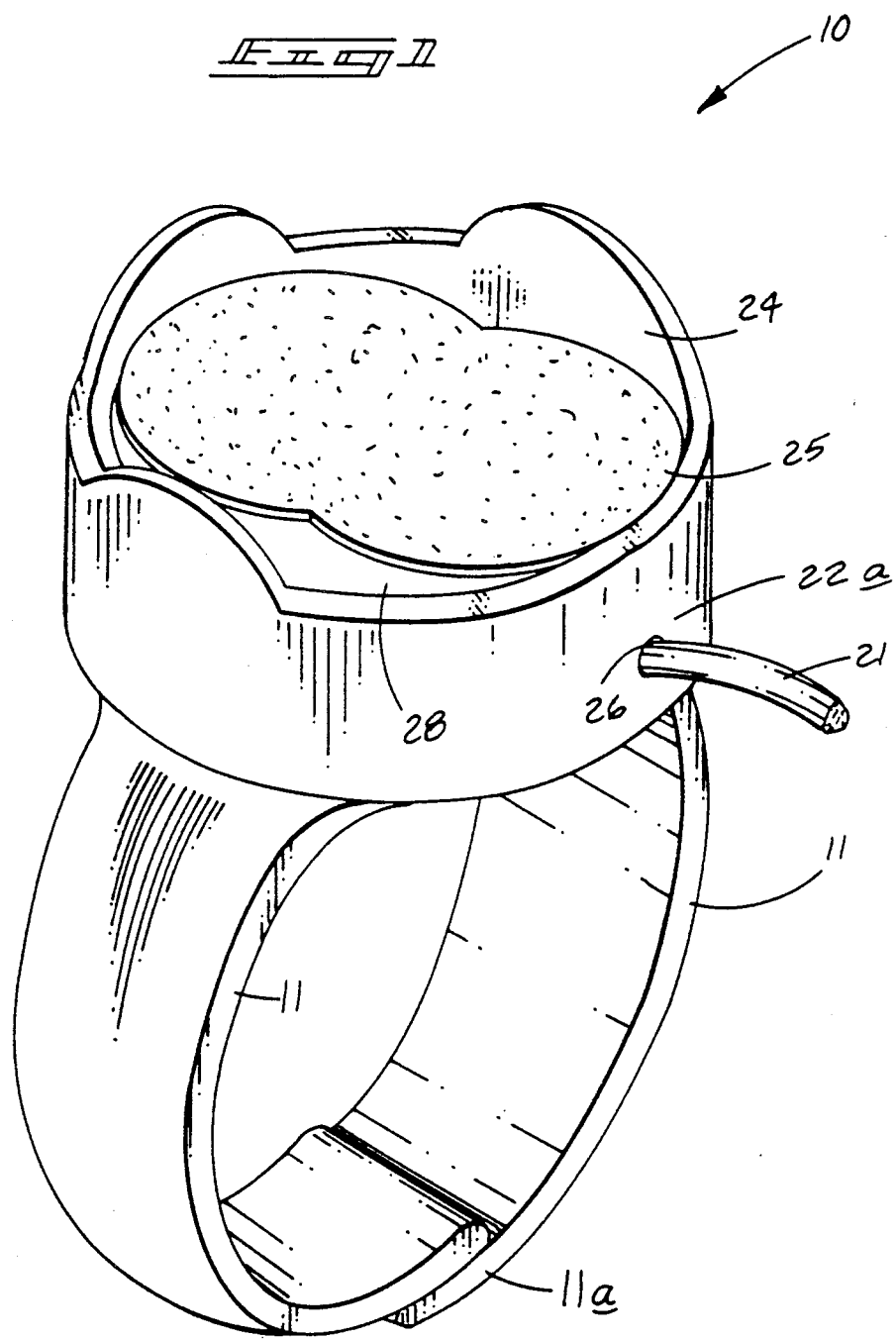
FIG. 1 is an isometric illustration of the instant invention.
Figure 2:
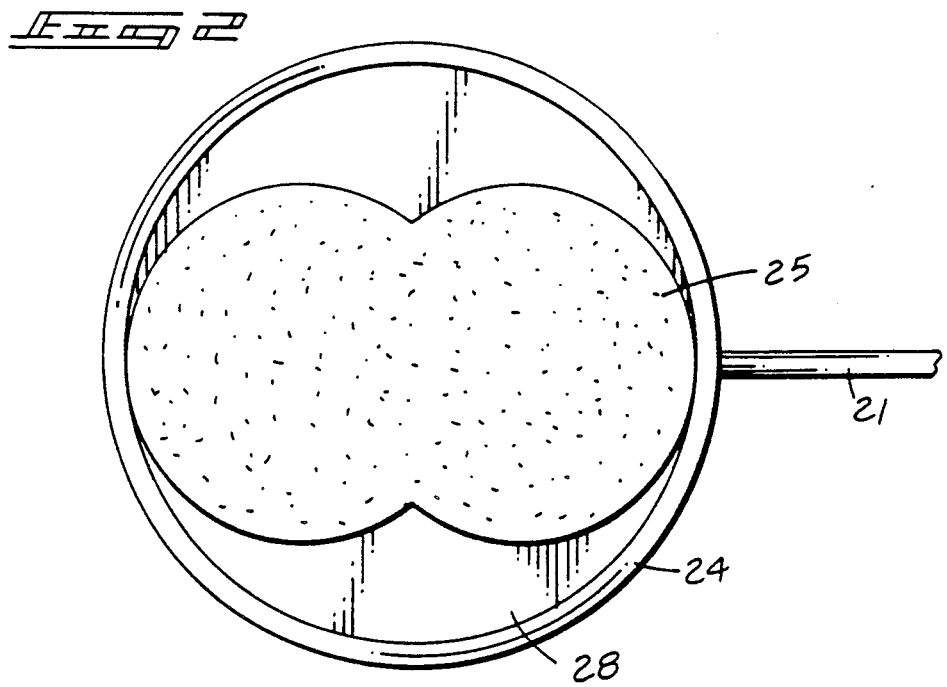
FIG. 2 is an orthographic top view of the instant invention.
Figure 3:
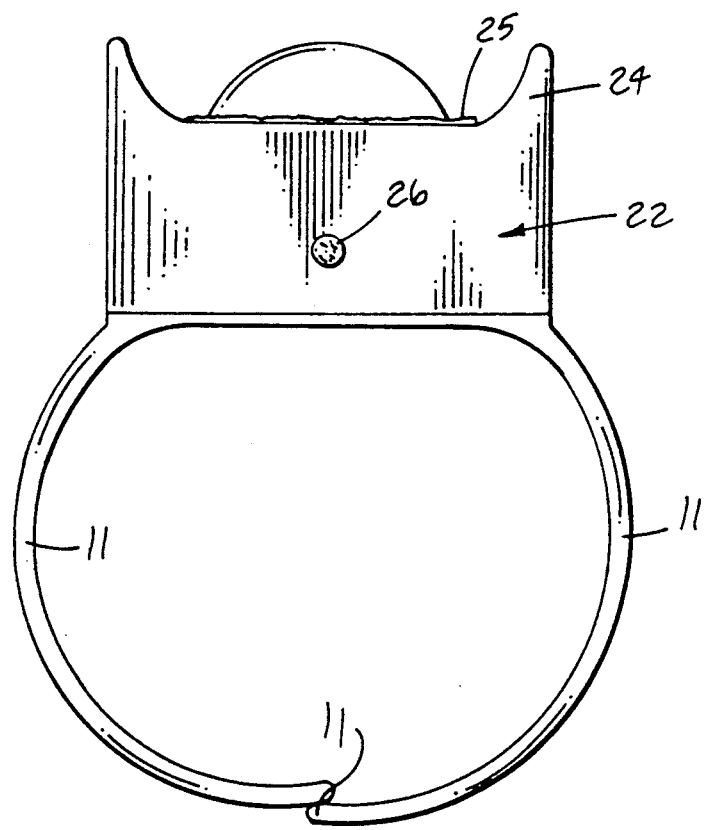
FIG. 3 is an orthographic frontal view, taken in elevation, of the instant invention.
Figure 6:
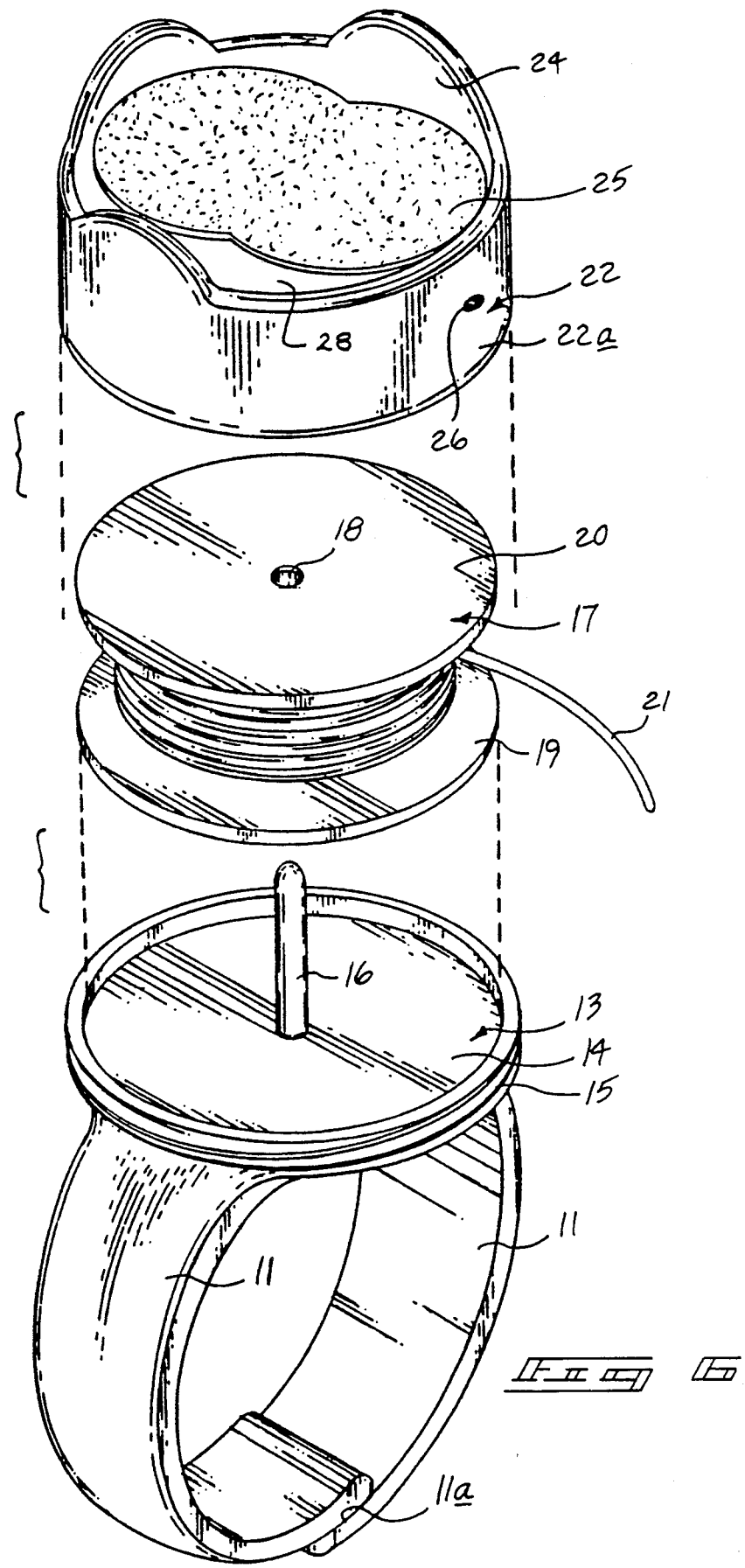
FIG. 6 is an isometric exploded illustration of the instant invention.

With reference now to the drawings, and in particular to FIGS. 1 to 6 thereof, a new and improved anxiety transference ring organization embodying the principles and concepts of the present invention and generally designated by the reference numeral 10 will be described.

More specifically, the anxiety transference ring organization 10 of the instant invention essentially comprises a plurality of semi-cylindrical leg member bands 11 defining an overlap 11a at lower terminal ends of the bands, wherein upper terminal ends of the bands 11 mount a ring support head 13. The ring support head 13 includes a planar top bearing surface 14 formed with an externally threaded cylindrical skirt 15 that extends above the bearing surface 14. A support post 16 is orthogonally and coaxially mounted relative to the planar top bearing surface 14 and extends above the bearing surface 14 a predetermined first height. A spool 17 is defined by a predetermined second height substantially equal to or less than the predetermined first height defined by the support post 16, and is defined by a lower cylindrical flange spaced from and parallel a top cylindrical flange 20 defined by a predetermined spacing substantially equal to the predetermined first height. Each of the flanges 19 and 20 are defined by a predetermined diameter substantially equal to a predetermined diameter defined by the bearing suface 14 to align and mount the lower flange 19 on the bearing surface 14. The spool 17 further includes a quantity of nylon fishing line 21 wound thereabout, whereupon the cap member 22, when secured to the support head 13, includes a line feed bore 26 projecting through the cap member 22 side wall 22a for permitting extraction of a predetermined quantity of the fishing line 21 permitting biting thereon by an individual in lieu of fingernail biting to provide transference of the biting habit to the fishing line rather than to destruction of an individual's fingernails. The side wall 22a is of cylindrical configuration and internally threaded securable to the externally threaded skirt 15. The cap member 22 includes a roof plate 28 parallel to and spaced from the bearing surface 14 a height equal to the predetermined first height to capture the spool 17 between the roof plate 28 and the bearing surface 14. The roof plate 28 includes a top surface mounting an abrasive plate 25 thereon confined within a top surface of the roof plate 28 and protected by a protective cylindrical side wall 24 of a serpentine configuration extending above the roof plate 28. The serpentine configuration permits ease of access of an individual's fingernail into various portions of the abrasive plate 25.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A ring organization for accomodating anxiety transference in lieu of nail biting. wherein the ring organization comprises, band means, including at least one leg band for securement of the at least one leg band about an individual's finger, wherein a ring support head is fixedly mounted to the band means, and the ring support head includes a planar top bearing surface, the planar top bearing surface is defined by a predetermined diameter and includes an externally threaded cylindrical skirt extending above the bearing surface, and a support post defined by a predetermined first height orthogonally and coaxially mounted to the planar top bearing surface, and a spool rotatably mounted on the bearing surface, wherein the spool is defined by a predetermined second height substantially equal to or less than the predetermined first height, and includes a through-extending bore coaxially directed through the spool for receiving the support post therethrough, and the spool mounting nylon fishing line wound thereabout, and wherein the spool is defined by a lower cylindrical flange spaced from and parallel a top cylindrical flange, wherein the lower and top cylindrical flanges are defined by a predetermined diameter substantially equal to the predetermined diameter of the bearing surface to align and mount the spool on the bearing surface, and further including a cap member, the cap member including a cylindrical internally threaded side wall, wherein the side wall is threadedly securable to the externally threaded cylindrical skirt, and the cap member including a roof plate, the roof plate spaced from and parallel to the bearing surface at a height equal to the predetermined first height when the cap member is mounted to the ring support head, and wherein the roof plate includes a top surface, and the top surface integrally mounts an abrasive plate thereon, wherein the abrasive plate is contained in the roof plate, and further including a protective cylindrical side wall coextensive with the cylindrical side wall extending above the roof plate defining a serpentine top edge to provide access to the abrasive plate through the protective cylindrical side wall.

* * * * *